(12) United States Patent
Kim et al.

(10) Patent No.: US 9,849,454 B2
(45) Date of Patent: Dec. 26, 2017

(54) MICROFLUIDIC CHIP AND REAL-TIME ANALYSIS DEVICE USING SAME

(71) Applicant: NANOBIOSYS INC., Seoul (KR)

(72) Inventors: Sung Woo Kim, Seoul (KR); Jae Young Byun, Anyang-si (KR); Duck Joong Kim, Anyang-si (KR)

(73) Assignee: NANOBIOSYS INC., Seoul (KR)

( * ) Notice: Subject to any disclaimer, the term of this patent is extended or adjusted under 35 U.S.C. 154(b) by 0 days.

(21) Appl. No.: 15/117,378

(22) PCT Filed: Feb. 9, 2015

(86) PCT No.: PCT/KR2015/001292
§ 371 (c)(1),
(2) Date: Aug. 8, 2016

(87) PCT Pub. No.: WO2015/119471
PCT Pub. Date: Aug. 13, 2015

(65) Prior Publication Data
US 2017/0021354 A1 Jan. 26, 2017

(30) Foreign Application Priority Data
Feb. 10, 2014 (KR) ........................ 10-2014-0015118

(51) Int. Cl.
*B01L 3/00* (2006.01)
*G01N 21/62* (2006.01)
(Continued)

(52) U.S. Cl.
CPC ........... *B01L 3/502723* (2013.01); *B01L 7/52* (2013.01); *G01N 21/6428* (2013.01);
(Continued)

(58) Field of Classification Search
CPC .. B01L 3/502723; B01L 3/5027; B01L 3/502; B01L 3/50; B01L 7/52; B01L 7/00
(Continued)

(56) References Cited

U.S. PATENT DOCUMENTS 4,595,561 A 6/1986 Thornton et al.
4,740,709 A 4/1988 Leighton et al.
(Continued)

FOREIGN PATENT DOCUMENTS

CN 101558289 A 10/2009
CN 102373153 A 3/2012
(Continued)

OTHER PUBLICATIONS

Zheng W. et al, Supporting Data for: A simple PDMS-based microfluidic channel design that removes bubbles from long-term on-chip culture of mammalian cells, The Royal Society of Chemistry, 2010, 201, pp. 1-7.*
(Continued)

*Primary Examiner* — Christine T Mui
(74) *Attorney, Agent, or Firm* — Novick, Kim & Lee, PLLC; Sang Ho Lee (57) ABSTRACT

The present invention relates to a microfluidic chip and a real-time analysis device using same, and more specifically, to a microfluidic chip and a real-time analysis device using same capable of securing reliability of measurement results by appropriately preventing reduction of optical signal sensitivity due to bubbles included in a fluid. According to one embodiment of the present invention, the microfluidic chip is provided. The microfluidic chip comprises: at least one reaction chamber which comprises at least one optical measuring area, and in which a random reaction of a fluid received therein takes place; and a bubble eliminating portion comprising a light transmitting material which pro-
(Continued)

trudes from an the inner surface of an upper part of the microfluidic chip toward the inside of the reaction chamber, to prevent bubbles included in the fluid from being included in the optical measuring area.

20 Claims, 5 Drawing Sheets (51) Int. Cl.
    *B01L 7/00* (2006.01)
    *G01N 21/64* (2006.01)
    *G01N 21/05* (2006.01)

(52) U.S. Cl.
    CPC ........ *G01N 21/6486* (2013.01); *B01L 3/5025* (2013.01); *B01L 2200/0684* (2013.01); *B01L 2200/10* (2013.01); *B01L 2300/0627* (2013.01); *B01L 2300/0809* (2013.01); *B01L 2300/0887* (2013.01); *B01L 2300/12* (2013.01); *G01N 2021/054* (2013.01)

(58) Field of Classification Search
    USPC .......................................... 422/502, 500, 50
    See application file for complete search history.

(56) References Cited

U.S. PATENT DOCUMENTS

| | | | |
|---|---|---|---|
| 6,537,505 B1 * | 3/2003 | LaBudde | F16K 31/0658 222/504 |
| 2006/0008382 A1 * | 1/2006 | Salamitou | B01L 3/502715 422/400 |
| 2008/0008628 A1 | 1/2008 | Park et al. | |
| 2008/0317632 A1 | 12/2008 | Shimasaki et al. | |
| 2009/0054255 A1 | 2/2009 | Lee et al. | |
| 2011/0044865 A1 * | 2/2011 | Groisman | B01L 9/527 422/503 |

FOREIGN PATENT DOCUMENTS

| | | |
|---|---|---|
| CN | 102806111 A | 12/2012 |
| JP | 50-089092 A | 7/1975 |
| JP | 2005-140652 A | 6/2005 |
| JP | 4252545 B2 | 4/2009 |
| JP | 2009-291758 A | 12/2009 |
| JP | 2009-544016 A | 12/2009 |
| JP | 2011-220996 A | 11/2011 |
| JP | 2013-019911 A | 1/2013 |
| KR | 10-1175594 B1 | 8/2012 |

OTHER PUBLICATIONS

Wenfu Zheng et al., "A simple PDMS-based microfluidic channel design that removes bubbles for long-term on-chip culture of mammalian cells", Lab on a Chip, Aug. 2, 2010, pp. 2906-2910.

* cited by examiner

MICROFLUIDIC CHIP AND REAL-TIME ANALYSIS DEVICE USING SAME

TECHNICAL FIELD

The present invention relates to a microfluidic chip and a real-time analysis device using the same, and more specifically, to a microfluidic chip and a real-time analysis device using the same capable of preventing reduction of optical signal sensitivity due to bubbles contained in a fluid, thereby securing reliability of measurement results.

BACKGROUND ART

A microfluidic chip functions to conduct various experiments at once by letting a fluid flow out through a microfluidic channel. In detail, after a microfluidic channel is manufactured using a material, such as plastic, glass, silicon, and so on, a fluid, for instance, a liquid sample, is moved through such a channel, and then, mixing, separation, refinement, reaction and analysis are executed in a plurality of chambers inside the microfluidic chip. Because various experiments which were conventionally executed in a laboratory are executed in the small chip, the microfluidic chip is also called "lab-on-a-chip".

The microfluidic chip can create cost and time reduction effects in the fields of pharmaceuticals, biotechnology, medicines and so on, and enhance accuracy, efficiency and reliability. For instance, compared with the conventional methods, the microfluidic chip can remarkably reduce the usage of protein and expensive reagents used for DNA analysis so as to show reduction effect of considerable expenses. Moreover, the microfluidic chip uses fewer amounts of protein samples or cell samples than the conventional methods, thereby reducing waste of samples.

In the meantime, the fluid used in the microfluidic chip may generate bubbles by micro cavities or pinholes formed inside the microfluidic chip while a reactive fluid, such as a sample reagent or a specimen, is injected. Particularly, the polymerase chain reaction (PCR) is executed using the microfluidic chip, the PCR accompanies a heat supply step, when the fluid is heated, the volume of small bubbles generated during injection is expanded to grow into bubbles of a larger size or a plurality of the small bubbles are joined together into one big bubble, so that a large quantity of bubbles are generated inside the fluid. If such bubbles are located in an optical measuring area, they may be a main cause to reduce optical signal sensitivity of a reaction product. Furthermore, if the bubbles move irregularly, it may cause decrease in reliability of the optical signal.

Figure 1:
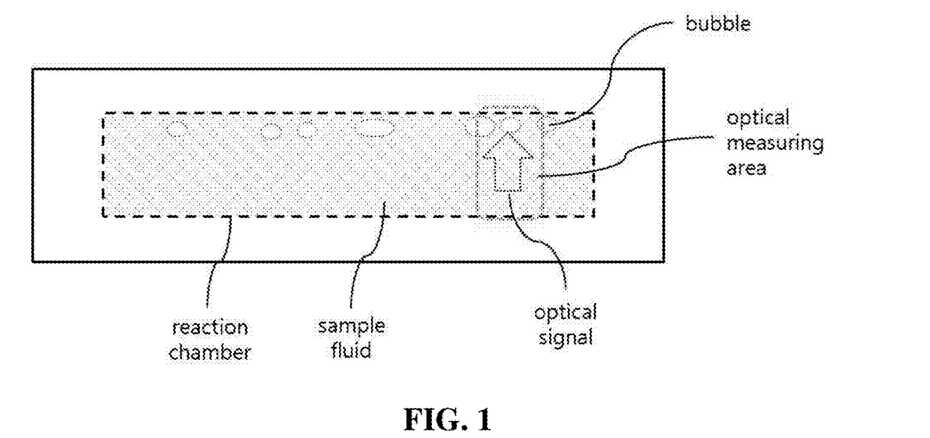
FIG. 1 is a view showing the phenomenon that an optical signal is reduced by bubbles contained in a fluid inside a microfluidic chip according to a prior art.

Referring to FIG. 1, optical signal sensitivity is decreased due to bubbles contained in the fluid during the process of reaction inside a conventional microfluidic chip. That is, because the miniaturized microfluidic chip has a space of a reaction chamber which is small for the size and the number of bubbles generated, there is high probability that the generated bubbles are located above any optical measuring area arranged in the reaction chamber. Additionally, as shown in FIG. 1, if bubbles are located inside the optical measuring area, the bubbles lower sensitivity of the optical signal because blocking the optical signal emitted from the reaction product.

Therefore, in order to realize miniaturization of the reaction chamber like the microfluidic chip, solutions to the problems arising from reduction and ununiformity of optical signal sensitivity in order to secure reliability of measurement results are required.

DISCLOSURE

Technical Problem

Accordingly, the present invention has been made in an effort to solve the above-mentioned problems occurring in the prior arts, and it is an object of the present invention to provide a microfluidic chip and a real-time analysis device using the same capable of preventing reduction of optical signal sensitivity due to bubbles contained in a fluid using a bubble-eliminating portion of a predetermined shape, thereby securing reliability of measurement results.

Technical Solution

To achieve the above objects, the present invention provides a microfluidic chip including: at least one reaction chamber in which any reaction to a fluid is executed and which includes at least one optical measuring area; and a bubble-eliminating portion which is made a light transmitting material and protrudes from an inner face of an upper part of the microfluidic chip toward the inside of the reaction chamber, in order to prevent bubbles contained in the fluid from interfering with the optical measuring.

Preferably, the bubble-eliminating portion is upwardly spaced apart from the bottom surface of the reaction chamber at a predetermined interval.

Moreover, preferably, the bubble-eliminating portion includes: a flat surface disposed in the middle of the bubble-eliminating portion; and an inclined surface connected with the inner face of the upper part of the microfluidic chip.

Furthermore, preferably, the bubble-eliminating portion includes a bubble collecting portion which is hollowed from at least an area of the bottom surface of the bubble-eliminating portion.

Additionally, preferably, the bubble-eliminating portion further includes a bubble collecting portion which is hollowed from the inner face of the upper part of the microfluidic chip along at least some of the circumference of the bubble-eliminating portion.

In addition, preferably, the microfluidic chip includes: a first plate of a flat type; a second plate of a flat type which is arranged on the first plate and has the reaction chamber; and a third plate which is arranged on the second plate and has the bubble-eliminating portion. Moreover, preferably, the third plate comprises an inlet and an outlet. The inlet and outlet are respectively connected with both ends of the reaction chamber.

Furthermore, preferably, at least some of the microfluidic chip is made of a plastic material with light transmitting property.

According to a preferred embodiment of the present invention, an analyzer is provided. The analyzer includes: the microfluidic chip; and an optical detection module which irradiates light to the microfluidic chip and detects an optical signal emitted from an optical measuring area of the microfluidic chip in order to measure reaction products contained in a reaction chamber in real time.

Advantageous Effects

As described above, the microfluidic chip according to the present invention can rapidly and accurately measure lots of reaction products of a small quantity at the same time without any problem arising from reduction and ununiformity of optical signal sensitivity in spite of microminiaturization of the microfluidic chip.

The microfluidic chip according to the present invention can effectively preclude formation of bubbles, which are contained in the fluid, out of the optical measuring area just by the structure formed inside the microfluidic chip.

MODE FOR INVENTION

Hereinafter, reference will be now made in detail to the preferred embodiment of the present invention with reference to the attached drawings. In the description of the present invention, when it is judged that detailed descriptions of known functions or structures related with the present invention may make the essential points vague, the detailed descriptions of the known functions or structures will be omitted. Hereinafter, exemplary embodiments of the present invention will be described in detail. However, the present invention is not limited to the embodiments disclosed below, but can be implemented in various forms by those skilled in the art.

Moreover, in the drawings, parts having similar functions and actions have the same reference numerals. In the description of the present invention, to connect some part with another part means that some part is directly connected with another part and that some part is indirectly connected with another part through an element. Furthermore, unless otherwise defined herein, to include a component does not mean that the mortise lock excludes other component but means that the mortise lock can include other components more.

Figure 2:
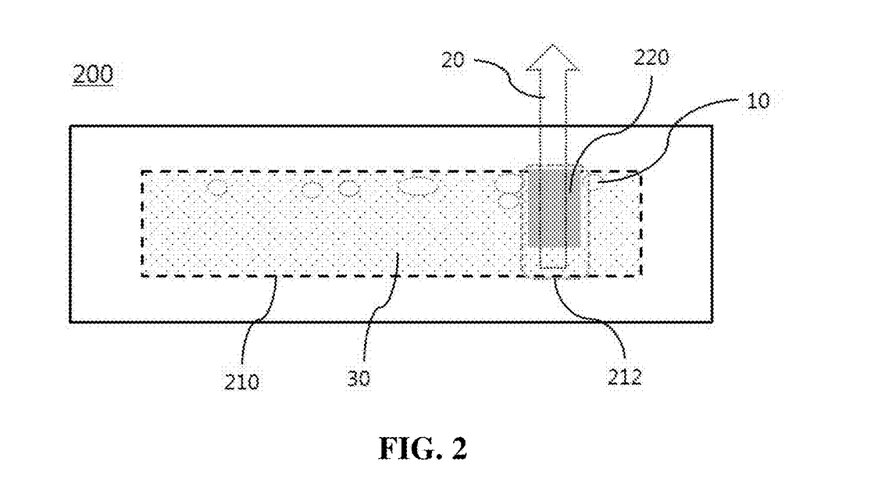
FIG. 2 is a view showing the basic configuration and the bubble elimination principle of a microfluidic chip according to a preferred embodiment of the present invention.

FIG. 2 is a view showing the basic configuration and the bubble-eliminating principle of a microfluidic chip according to a preferred embodiment of the present invention.

Referring to FIG. 2, the microfluidic chip according to the preferred embodiment of the present invention includes: a reaction chamber 210 which executes a reaction; and a bubble-eliminating portion 220 protruding from an inner face of an upper part of the microfluidic chip 200 toward the inside of the reaction chamber 210.

The reaction chamber 210 accommodates a fluid 30, such as a sample reagent or a specimen, therein in order to execute a reaction adequate for an experiment purpose, and includes at least one optical measuring area 212. Here, the optical measuring area 212 may be defined as a target area on the reaction chamber 210 in which an optical signal 20 emitted from a reaction product is detected in order to measure results of a reaction executed inside the reaction chamber 210 in real time.

In this instance, the reaction chamber 210 must be suitable for executing a reaction serving an experimental purpose, and especially, the microfluidic chip 200 in which PCR is executed must be implemented not to be influenced by repeated heating and cooling during the PCR process. Therefore, the microfluidic chip 200 is not restricted by specific shapes and/or materials if it can maintain such a function. However, because the microfluidic chip 200 according to the preferred embodiment of the present invention premises a real time optical signal measurement of the reaction product, it is preferable that at least a portion which is overlapped with the route of the optical signal 20 emitted from the optical measuring area 212 be made of a light transmitting material.

The bubble-eliminating portion 220 is to prevent bubbles 10 contained in a fluid 30 from interfering with the optical measuring area 212. As shown in FIG. 2, the bubble-eliminating portion 220 may have a predetermined shape formed by protruding from the inner face of the upper part of the microfluidic chip 200 to the inside of the reaction chamber 210. At least a part of the bubble-eliminating portion 220 passes through the surface of the fluid 30 and is spaced apart from the bottom surface of the reaction chamber 210 at a predetermined interval to be submerged under the fluid 30. Additionally, the bubble-eliminating portion 220 may have one of various protruding shapes, but it is preferable to be formed in a cylindrical shape or a square pillar shape. In this instance, the bubble-eliminating portion 220 is made of a light transmitting material, and at least a part of the bubble-eliminating portion 220 may be included in the optical measuring area 212. Therefore, the optical signal 20 generated from the reaction product inside the optical measuring area 212 passes the bubble-eliminating portion 22, and then, is emitted out of the microfluidic chip 200.

As described above, the bubble-eliminating portion 220 prevents bubbles 10 inside the fluid 30 from interfering with optical measuring area 212 so as to increase optical signal sensitivity. In detail, because some of the bubble-eliminating portion 220 having the predetermined shape is located in the state where it is submerged under the fluid 30, the bubbles 10 included in the fluid 30 are pushed to spaces around the optical measuring area 212 by buoyancy of the bubbles 10 to rise above the fluid 30. Therefore, the bubbles 10 deviate from the emission route of the optical signal 20 emitted from the reaction product existing on the optical measuring area 212, and do not have any influence on optical signal sensitivity required to measure the reaction product in real time.

Therefore, if the reaction product inside the reaction chamber 210 is measured in real time using the microfluidic chip 20 according to the preferred embodiment of the present invention, the microfluidic chip according to the present invention can rapidly and accurately measure lots of reaction products of a small quantity at the same time while there is little adverse influence by the bubbles 10 generated inside the reaction chamber 210 in spite of microminiaturization of the microfluidic chip 200.

Figure 3:
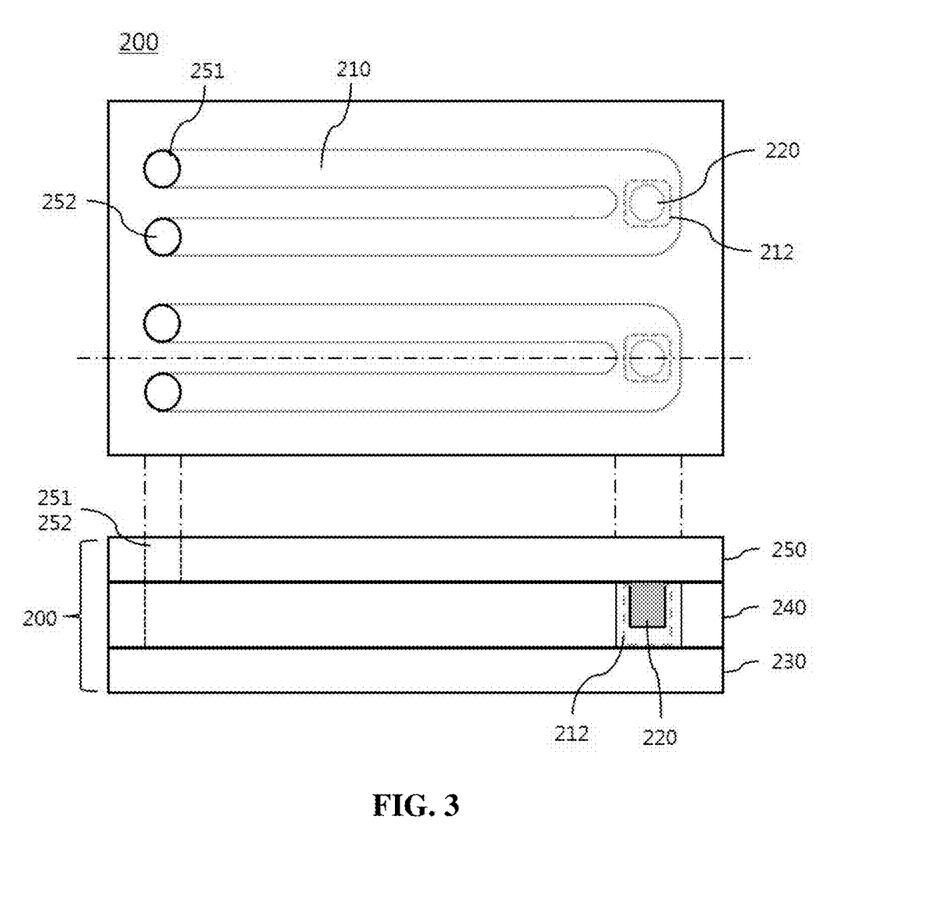
FIG. 3 is a detailed view of the configuration of the microfluidic chip according to the preferred embodiment of the present invention.

FIG. 3 is a detailed view of the configuration of the microfluidic chip according to the preferred embodiment of the present invention.

Referring to FIG. 3, the microfluidic chip 200 according to the preferred embodiment of the present invention may include at least one reaction chamber 210. FIG. 3 illustrates two reaction chambers 210, but the microfluidic chip 200 according to the present invention may include two or more reaction chambers 210 according to the use purpose and scope of the microfluidic chip 200. In the meantime, as shown in FIG. 3, the reaction chamber 210 is bent in the form of the letter 'U' at the central area in such a way that both ends of the reaction chamber 210 are located on the same vertical line. In this instance, the bubble-eliminating portion 220 and the optical measuring area 212 are located on the bent central area of the reaction chamber 210. FIG. 3 illustrates the form of the reaction chamber and the locations of the bubble-eliminating portion 220 and the optical measuring area 212 on the reaction chamber 210, but they are not restricted to the above and may be varied according to embodiments of the present invention.

Referring to FIG. 3, the configuration of the microfluidic chip 200 according to the preferred embodiment of the present invention will be described in more detail. The microfluidic chip 200 includes: a first plate 230 of a flat type; a second plate 240 of a flat type which is arranged on the first plate 230 and has the reaction chamber 210; and a third plate 250 which is arranged on the second plate 240 and has the bubble-eliminating portion 220.

The first plate 230 is formed in a flat type and serves as a floor support of the microfluidic chip 200 according to the preferred embodiment of the present invention. The first plate 230 may be made of various materials, and preferably, is made of a material selected from the group consisting of polydimethylsiloxane (PDMS), cyclo-olefin copolymer (COC), polymethylmetharcylate (PMMA), polycarbonate (PC), polypropylene carbonate (PPC), polyether sulfone (PES), polyethylene terephthalate (PET), and a combination thereof. According to embodiments, at least a part of the first plate 230 may be made of a light transmitting material. Moreover, according to embodiments, the surface of the first plate 230 may be treated to have hydrophilic surface property. In this instance, the hydrophilic substance includes various materials, and preferably, includes a material selected from the group consisting of carboxyl group (—COOH), amine group (—NH2), hydroxyl group (—OH), and sulfone group (—SH). The treatment of the hydrophilic substance is conducted in a manner known in the art.

The second plate 240 is arranged on the first plate 230 and serves to form the reaction chamber 210 of the microfluidic chip 200. The second plate 240 may be made of various materials, and preferably, it is made of thermoplastic resin or thermosetting resin selected from the group consisting of polymethylmetharcylate (PMMA), polycarbonate (PC), cyclo-olefin copolymer (COC), polyamide (PA), polyethylene (PE), polypropylene (PP), polyphenylene ether (PPE), polystyrene (PS), polyoxymethylene (POM), polyetheretherketone (PEEK), polytetrafluoroethylene (PTFE), polyvinylchloride (PVC), polyvinylidene fluoride (PVDF), polybutyleneterephthalate (PBT), fluorinated ethylenepropylene (FEP), perfluoralkoxyalkane (PFA), and a combination thereof. According to embodiments, at least a part of the second plate 240 may be made of a light transmitting material. In the meantime, according to embodiments, the inner wall of the second plate 240 may be coated with a material like silane group, bovine serum albumin (BSA) and so on, so as to prevent protein from being absorbed thereonto. The treatment of the material is conducted in a manner known in the art.

The third plate 250 is arranged on the second plate 240 and serves as a cover for covering the reaction chamber 210. The bubble-eliminating portion 220 located on the bottom surface of the third plate 250 is formed to protrude toward the inside of the reaction chamber 210. The third plate 250 may be made of various materials, and preferably, is made of a material selected from the group consisting of polydimethylsiloxane (PDMS), cyclo-olefin copolymer (COC), polymethylmetharcylate (PMMA), polycarbonate (PC), polypropylene carbonate (PPC), polyether sulfone (PES), polyethylene terephthalate (PET), and a combination thereof. According to embodiments, at least a part of the third plate 250 may be made of a light transmitting material. In the meantime, the third plate 250 includes an inlet 251 and an outlet 252 which are respectively connected with both ends of the reaction chamber 210. A sample reagent or a specimen for executing a reaction is injected through the inlet 251, and the fluid 30 is discharged out through the outlet 252 after the reaction is finished. According to embodiments, the inlet 251 and the outlet 252 may include covering means (not shown) in order to prevent a solution leak when the reaction to the fluid 30 is executed inside the reaction chamber 210. Such covering means may be manufactured in various shapes and sizes and made of various materials.

Meanwhile, according to embodiments, the first plate 230, the second plate 240 and the third plate 250 which are formed individually are bonded mutually, or two of the three plates 230, 240 and 250 are formed integrally and the other one is bonded to the two plates. For instance, the first plate 230 and the second plate 240 are formed integrally and the third plate 250 is bonded to the first and second plates, or the second plate 240 and the third plate 250 are formed integrally and the first plate 230 is bonded to the second and third plates. In this instance, the first plate 230, the second plate 240 and the third plate 250 may be bonded together by various methods for bonding which are applicable in the relevant field, such as thermal shrinking, thermosonic bonding, ultraviolet bonding, solvent bonding, tape lamination and so on.

Figure 4:
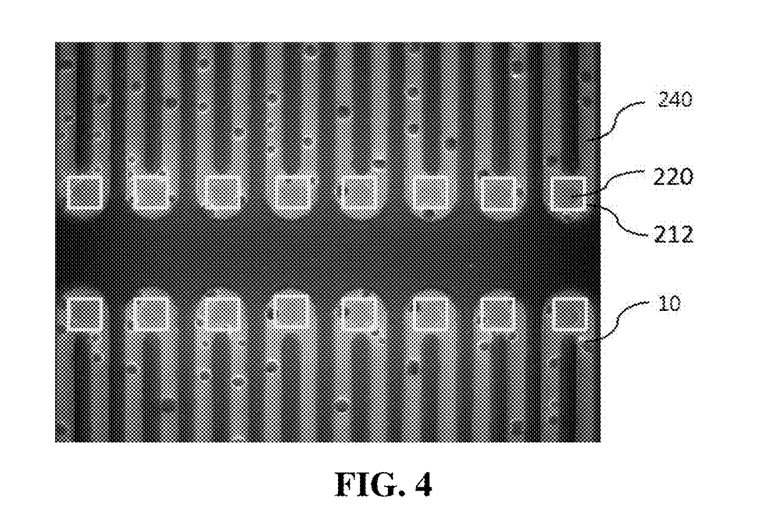
FIG. 4 is a photofluorogram of the microfluidic chip according to the preferred embodiment of the present invention.

FIG. 4 is a photofluorogram of the microfluidic chip according to the preferred embodiment of the present invention.

As shown in FIG. 4, a plurality of the reaction chambers 210 are formed on the microfluidic chip 200 according to the preferred embodiment of the present invention in order to measure a plurality of reaction products at the same time. Moreover, the optical measuring area 212 and the bubble-eliminating portion 220 which is arranged inside the optical measuring area 212 are located at some area of each reaction chamber 210, preferably, at the bent central area of the reaction chamber 210.

Referring to FIG. 4, the bubbles 10 contained inside the reaction chamber 210 are effectively eliminated from each optical measuring area 212 by the bubble-eliminating portion 220 existing in the optical measuring area 212 of each reaction chamber 210. In other words, the bubbles 10 are moved to the spaces around the optical measuring area 212 so as to deviate from the emission route of the optical signal 20 emitted from the optical measuring area 212.

As described above, the microfluidic chip 200 according to the preferred embodiment of the present invention can secure reliability of the measurement results to the reaction products because being not affected by the bubbles 10 generated inside the reaction chamber 210.

Figure 5:
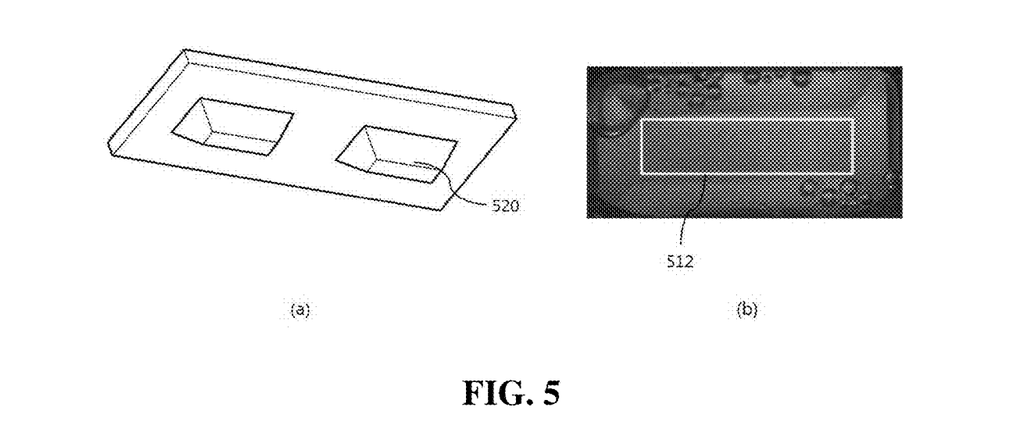
FIGS. 5 to 7 illustrate various embodiments of a bubble-eliminating portion of the microfluidic chip according to the preferred embodiment of the present invention.
Figure 6:
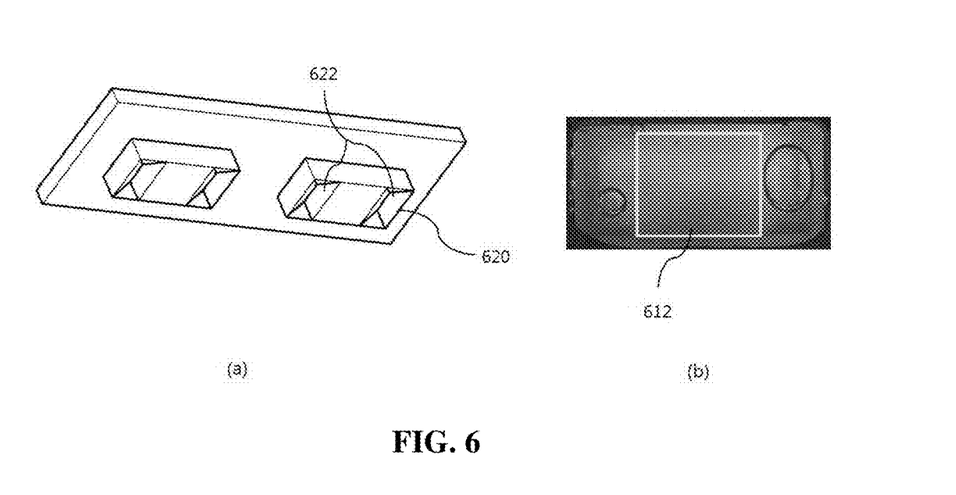
Figure 7:
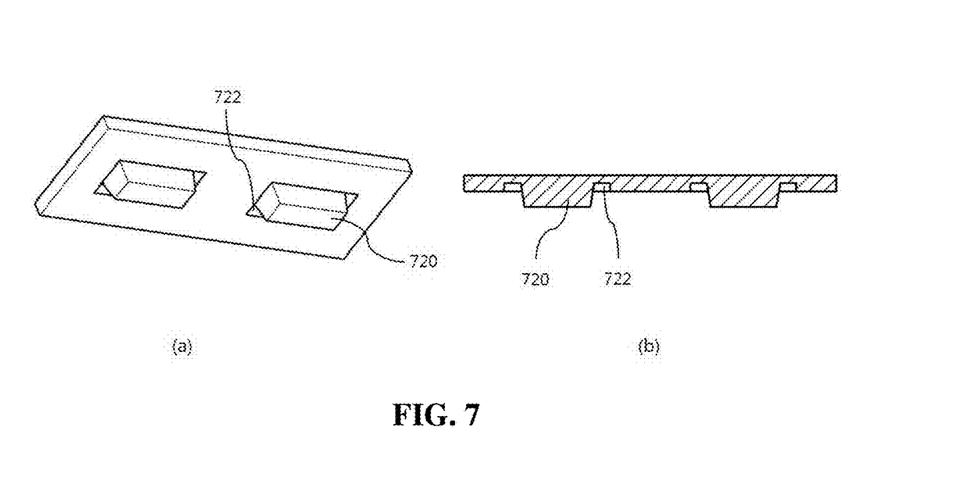

FIGS. 5 to 7 illustrate various embodiments of a bubble-eliminating portion of the microfluidic chip according to the preferred embodiment of the present invention. In the meantime, for convenience in description, FIGS. 5 to 7 illustrate only the bubble-eliminating portion and some of the microfluidic chip having the bubble-eliminating portion.

First, referring to FIG. 5(a), the bubble-eliminating portion 520 includes: a flat surface disposed in the middle of the bubble-eliminating portion 520; and an inclined surface connected with the inner face of the upper part of the microfluidic chip. As described above, if the side of the bubble-eliminating portion 520 is the inclined surface, the bubbles 10 move upward from the reaction chamber along the inclined surface so as to more easily move toward the spaces around the optical measuring area 512. In this instance, as shown in FIG. 5(b), the optical measuring area 512 may be an area on the reaction chamber on which the flat surface of the bubble-eliminating portion 520 is located so that the bubbles 10 are not contained.

Furthermore, referring to FIG. 6(a), the bubble-eliminating portion 620 may include a bubble collecting portion 622 which is hollowed from at least an area of the bottom surface, namely, at least an area of a portion adjacent to the bottom surface. Because the surface of the portion where the bubble collecting portion 622 is formed is located higher inside the reaction chamber than a portion where the bubble collecting portion 622 is not formed, as shown in FIG. 6(b), the bubbles 10 pushed out of the central portion of the bubble-eliminating portion 620 can be collected on the bubble collecting portion 622. In this instance, as shown in FIG. 6(b), the optical measuring area 612 may be an area on the reaction chamber on which the portion of the bubble-eliminating portion 620 where the bubble collecting portion 622 is not formed is located.

In the meantime, as shown in FIG. 7, the bubble collecting portion 722 may be formed along the circumference of the bubble-eliminating portion 720. That is, the bubble collecting portion 722 may be formed to be hollowed from the inner face of the upper part of the microfluidic chip toward the upward direction along at least some of the circumference of the protruding bubble-eliminating portion 720. In this instance, not shown in FIG. 7, but similarly with the description referring to FIG. 6, the bubbles 10 pushed out by the bubble-eliminating portion 720 are collected on the bubble collecting portion 722 which is hollowed.

Meanwhile, according to an embodiment of the present invention, an analyzer may be provided. Referring to FIGS. 2 and 3, the analyzer includes: the microfluidic chip 200 according to the embodiment of the present invention; and an optical detection module. The optical detection module is a device to irradiate light to the microfluidic chip 200 and detect an optical signal 20 emitted from the optical measuring area 212. Various optical detection modules applicable in the technical fields to which the present invention belongs can be used. For instance, the optical detection module includes: a light source arranged to supply light to the reaction chamber 210 of the microfluidic chip 200; and an optical detecting part arranged to receive light emitted from the reaction chamber 210. The light source and the optical detecting part are arranged across the reaction chamber 210 from each other (transmission type) or are all arranged in one direction of the reaction chamber 210 (reflection type).

Figure 8A:
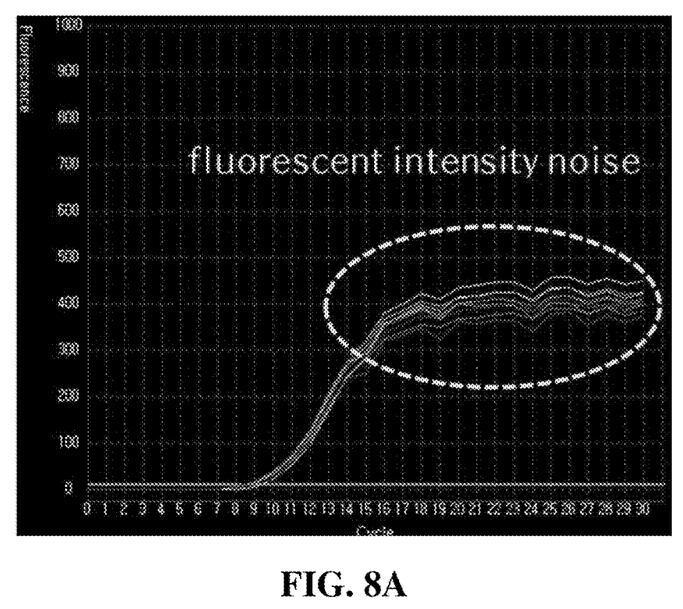
FIGS. 8a and 8b are comparative examples showing measurement results of reaction products executed using the microfluidic chip according to the prior art, which has no bubble-eliminating portion, and the microfluidic chip according to the present invention.
Figure 8B:
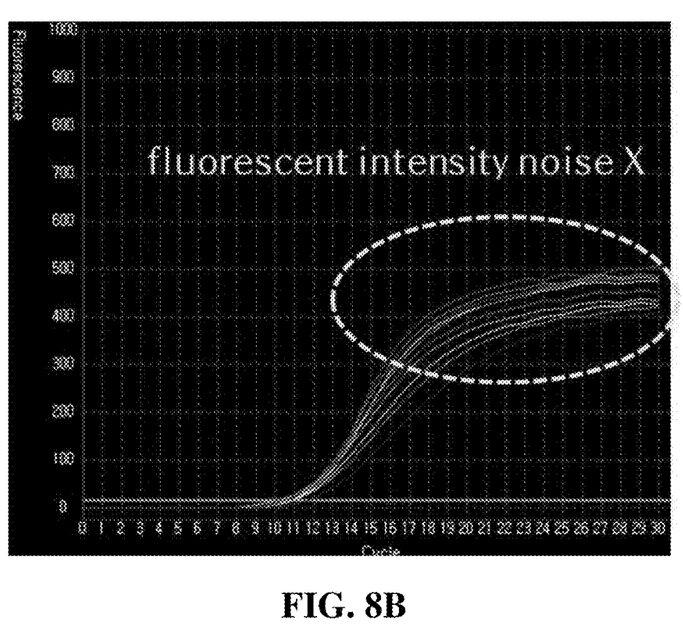

FIGS. 8a and 8b are comparative examples showing measurement results of reaction products executed using the microfluidic chip according to the prior art, which has no bubble-eliminating portion, and the microfluidic chip according to the present invention.

In detail, samples and reagents for PCR were injected into the conventional microfluidic chip which had no bubble-eliminating means and the microfluidic chip 200 implemented according to FIG. 3, and then, PCR was executed. Nucleic acid amplification results were measured through the optical detection module while PCR was executed, and the results were checked through a graph on real-time PCR results (X-axis is the number of cycles, and Y-axis is fluorescence).

FIG. 8a illustrates real-time PCR measurement results using the conventional microfluidic chip which has no bubble-eliminating means, and FIG. 8b illustrates real-time PCR measurement results using the microfluidic chip 200 according to the present invention. As shown in FIGS. 8a and 8b, when real-time PCR was executed using the microfluidic chip 200 according to the present invention, differently from the conventional microfluidic chip generating lots of noise, the microfluidic chip 200 according to the present invention could effectively eliminate noise included in the detected optical signal.

As described above, the optimum embodiments have been shown and described in the drawings and in the specification. Here, specific terms have been used, but the terms are not used to limit the meanings or restrict the technical scope of the present invention described in the claims but are just used to describe the present invention. Therefore, it will be understood by those of ordinary skill in the art that various changes, modifications and equivalents may be made therein without departing from the spirit and scope of the present invention as defined by the following claims.

The invention claimed is:

1. A microfluidic chip comprising:
   an upper part;
   a bottom part; and
   at least one reaction chamber defined between the upper part and the bottom part, wherein the at least one reaction chamber holds a fluid and has an optical measuring area,
   wherein
   the upper part comprises a bubble-eliminating portion made of a light-transmitting material,
   the bubble-eliminating portion protrudes in a direction to the bottom part,
   at least a part of a distal end of the bubble-eliminating portion is covered and is spaced apart from the bottom part, and
   at least a part of the distal end of the bubble-eliminating portion is overlapped with the optical measuring area of the reaction chamber.

2. The microfluidic chip according to claim 1, wherein the bubble-eliminating portion is located in an optical path between a light-emitting module and a light-detecting module for detecting optical signals in said fluid.

3. The microfluidic chip according to claim 1, wherein at least a part of the microfluidic chip is made of a light-transmitting material.

4. The microfluidic chip according to claim 3, wherein the optical measuring area is at or near the center of the reaction chamber and is made of a light-transmitting material.

5. The microfluidic chip according to claim 2, wherein:
   the reaction chamber further comprises one or more optical measuring areas, and
   the upper part further comprises one or more bubble-eliminating portions, each corresponding to each of the one or more optical measuring areas.

6. The microfluidic chip according to claim 2, wherein the part of the distal end of the bubble-eliminating portion is spaced apart from the bottom part at a predetermined interval.

7. The microfluidic chip according to claim 6, wherein the bubble-eliminating portion comprises:
- a flat surface disposed on the distal end of the bubble-eliminating portion; and
- an inclined surface extended from the flat surface to the upper part of the microfluidic chip.

8. The microfluidic chip according to claim 6, wherein the bubble-eliminating portion is in a cylindrical shape or a square pillar shape.

9. The microfluidic chip according to claim 2, wherein the bubble-eliminating portion comprises,
- a flat surface disposed on the distal end of the bubble-eliminating portion;
- a wall extended from the flat surface to the upper part of the microfluidic chip; and
- a first bubble-collecting part which is hollowed in an opposite direction from the bottom part and located at a part of the distal end of the bubble-eliminating portion, wherein the first bubble-collecting part is not overlapped with the optical measuring area.

10. The microfluidic chip according to claim 2, further comprising a flat surface disposed on the distal end of the bubble-eliminating portion and a wall extended from the flat surface to the upper part of the microfluidic chip, wherein the upper part has a second bubble-collecting part which is hollowed in an opposite direction from the bottom part and located at an area where the wall meets the upper part along at least a part of the circumference of the bubble-eliminating portion, and wherein the second bubble-collecting part is not overlapped with the optical measuring area.

11. The microfluidic chip according to claim 2, wherein the bottom part is a plate having a flat-plate shape and the upper part is a plate having a flat-plate shape.

12. The microfluidic chip according to claim 11, wherein the bottom part is made of a material selected from the group consisting of polydimethylsiloxane (PDMS), cyclo-olefin copolymer (COC), polymethylmetharcylate (PMMA), polycarbonate (PC), polypropylene carbonate (PPC), polyether sulfone (PES), polyethylene terephthalate (PET), or a combination thereof.

13. The microfluidic chip according to claim 11, wherein the upper part is made of made of a material selected from the group consisting of polydimethylsiloxane (PDMS), cyclo-olefin copolymer (COC), polymethylmetharcylate (PMMA), polycarbonate (PC), polypropylene carbonate (PPC), polyether sulfone (PES), polyethylene terephthalate (PET), or a combination thereof.

14. The microfluidic chip according to claim 11, further comprising a middle plate that houses the at least one reaction chamber of the microfluidic chip and is sandwiched between the upper part and the bottom part.

15. The microfluidic chip according to claim 14, wherein the middle plate is made of thermoplastic resin or thermosetting resin selected from the group consisting of polymethylmetharcylate (PMMA), polycarbonate (PC), cyclo-olefin copolymer (COC), polyamide (PA), polyethylene (PE), polypropylene (PP), polyphenylene ether (PPE), polystyrene (PS), polyoxymethylene (POM), polyetheretherketone (PEEK), polytetrafluoroethylene (PTFE), polyvinylchloride (PVC), polyvinylidene fluoride (PVDF), polybutyleneterephthalate (PBT), fluorinated ethylenepropylene (FEP), perfluoralkoxyalkane (PFA), or a combination thereof.

16. The microfluidic chip according to claim 14, wherein:
- the upper part and the middle plate are bonded by thermal shrinking, thermosonic bonding, ultraviolet bonding, solvent bonding, tape lamination, or a combination thereof, and/or
- the middle plate and the bottom part are bonded by thermal shrinking, thermosonic bonding, ultraviolet bonding, solvent bonding, tape lamination, or a combination thereof.

17. The microfluidic chip according to claim 14, wherein the bottom part, the middle plate, and the bottom part, individually, are partially made of a light-transmitting material.

18. The microfluidic chip according to claim 11, wherein the upper part further comprises an inlet and an outlet which are respectively connected with both ends of the reaction chamber.

19. The microfluidic chip according to claim 18, wherein:
- the inlet and the outlet each comprise a cover, and
- said fluid in the reaction chamber is added through the inlet and discharged through the outlet.

20. An analyzer comprising:
- a microfluidic chip comprising,
  - an upper part;
  - a bottom part; and
  - at least one reaction chamber defined between the upper part and the bottom part, wherein the at least one reaction chamber holds a fluid and has an optical measuring area, wherein the upper part comprises a bubble-eliminating portion made of a light-transmitting material, the bubble-eliminating portion protrudes in a direction to the bottom part, at least a part of a distal end of the bubble-eliminating portion is covered and is spaced apart from the bottom part, and at least the part of the distal end of the bubble-eliminating portion is overlapped with the optical measuring area of the reaction chamber;
- the light-emitting module; and
- the light-detecting module for monitoring optical signals in said fluid in the reaction chamber in real time,
- wherein the bubble-eliminating portion is located in an optical path between a light-emitting module and a light-detecting module.

* * * * *